(12) United States Patent
Finke

(10) Patent No.: US 8,286,791 B2
(45) Date of Patent: Oct. 16, 2012

(54) SYRINGE ASSEMBLY CARRIER

(75) Inventor: Melvin Finke, DeLand, FL (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/894,487

(22) Filed: Sep. 30, 2010

(65) Prior Publication Data

US 2012/0080342 A1    Apr. 5, 2012

(51) Int. Cl.
*B65D 83/10* (2006.01)
*B65D 85/20* (2006.01)
*A47F 7/00* (2006.01)

(52) U.S. Cl. ............................ 206/366; 206/439; 211/74

(58) Field of Classification Search ................. 206/366, 206/438, 439, 365; 211/60.1, 74, 85.13
See application file for complete search history.

(56) References Cited

U.S. PATENT DOCUMENTS

| | | | | |
|---|---|---|---|---|
| 2,557,420 | A * | 6/1951 | Elliott | 206/366 |
| 4,106,622 | A * | 8/1978 | Windischman | 206/365 |
| 4,166,533 | A * | 9/1979 | Maitland | 206/366 |
| 4,892,525 | A * | 1/1990 | Hermann et al. | 206/365 |
| 5,519,931 | A * | 5/1996 | Reich | 206/365 |
| 5,934,859 | A | 8/1999 | Goetzelmann | |
| 6,164,044 | A | 12/2000 | Porfano et al. | |
| 6,189,292 | B1 * | 2/2001 | Odell et al. | 53/425 |
| 6,566,144 | B1 | 5/2003 | Madril et al. | |
| 6,719,141 | B2 * | 4/2004 | Heinz et al. | 206/443 |
| 6,907,679 | B2 * | 6/2005 | Yarborough et al. | 34/285 |
| 7,104,400 | B2 | 9/2006 | Kiehne | |
| 7,428,807 | B2 | 9/2008 | Vander Bush et al. | |
| 7,431,157 | B2 * | 10/2008 | Porret et al. | 206/366 |
| 7,963,396 | B2 * | 6/2011 | Vanderbush et al. | 206/366 |
| 2002/0069616 | A1 | 6/2002 | Odell et al. | |
| 2007/0151882 | A1 * | 7/2007 | Cocheteux et al. | 206/366 |
| 2008/0244923 | A1 | 10/2008 | Yarborough et al. | |
| 2009/0004063 | A1 | 1/2009 | Higashihara et al. | |
| 2009/0100802 | A1 | 4/2009 | Bush et al. | |
| 2009/0232966 | A1 | 9/2009 | Kalyankar et al. | |

FOREIGN PATENT DOCUMENTS

WO    WO 99/06100    2/1999

OTHER PUBLICATIONS

European Search Report in copending European Application No. 11007638.7 dated Feb. 2, 2012.

* cited by examiner

*Primary Examiner* — Bryon Gehman
(74) *Attorney, Agent, or Firm* — Lisa E. Winsor, Esq.

(57) ABSTRACT

A syringe assembly carrier includes a syringe-well holding fixture, a plurality of openings defined in the syringe-well holding fixture, and a plurality of syringe wells. Each of the syringe wells is configured to removeably receive a syringe assembly. The syringe-well holding fixture includes an upper surface and a plurality of mounting flanges coupled to the upper surface. Each of the plurality of mounting flanges is individually associated with a different opening in the syringe-well holding fixture and configured to receive a syringe well.

9 Claims, 3 Drawing Sheets

SYRINGE ASSEMBLY CARRIER

BACKGROUND

1. Technical Field

The present disclosure relates to syringes and, more particularly, to medical syringe assemblies such as disposable syringes and prefilled syringes, which include a selectively attachable/detachable plunger rod, and syringe assembly carriers suitable for syringe filling and distribution of syringe assemblies.

2. Discussion of Related Art

A conventional syringe typically includes a hollow barrel configured to slideably receive a plunger having a piston supported on a distal end thereof. The plunger is received in the hollow barrel and partially extends through a proximal end thereof. In use, as the plunger is translated relative to the hollow barrel, the piston is also translated to thereby aspirate and/or dispense fluid into/out of the hollow barrel.

Syringes have been developed for use as disposable syringes that are discarded after a single administration and which include a selectively attachable/detachable plunger assembly. A single-use syringe prevents reuse of the syringe to minimize exposure of patients to HIV, hepatitis and other blood-borne pathogens.

In the case of pre-filled syringes, the syringe is provided with a barrel containing a fluid and with the plunger pre-attached to the barrel. In the instance of relatively large prefilled syringes, the portion of the plunger extending from the barrel may be relatively large. To reduce the overall length of the pre-filled barrel and plunger, pre-filled syringes have been developed wherein the plunger is selectively attachable/detachable to/from the piston. In this manner, syringes including pre-filled barrels and separate plungers may be stored and shipped at reduced costs.

SUMMARY

A need exists for an improved syringe assembly carrier which provides a structured configuration to simplify sterilization, distribution and presentation of the syringe assemblies to automated syringe-filling operations.

The present disclosure relates to a syringe assembly carrier including a syringe-well holding fixture, a plurality of openings defined in the syringe-well holding fixture, and a plurality of syringe wells. Each of the syringe wells is configured to removeably receive a syringe assembly. The syringe-well holding fixture includes an upper surface and a plurality of annular mounting flanges coupled to the upper surface. Each of the plurality of annular mounting flanges is individually associated with a different opening in the syringe-well holding fixture and configured to receive a syringe well.

BRIEF DESCRIPTION OF THE DRAWINGS

Objects and features of the presently-disclosed syringe assemblies and syringe assembly carriers suitable for syringe filling and distribution of syringe assemblies will become apparent to those of ordinary skill in the art when descriptions of various embodiments thereof are read with reference to the accompanying drawings, of which.

DETAILED DESCRIPTION

Figure 1:
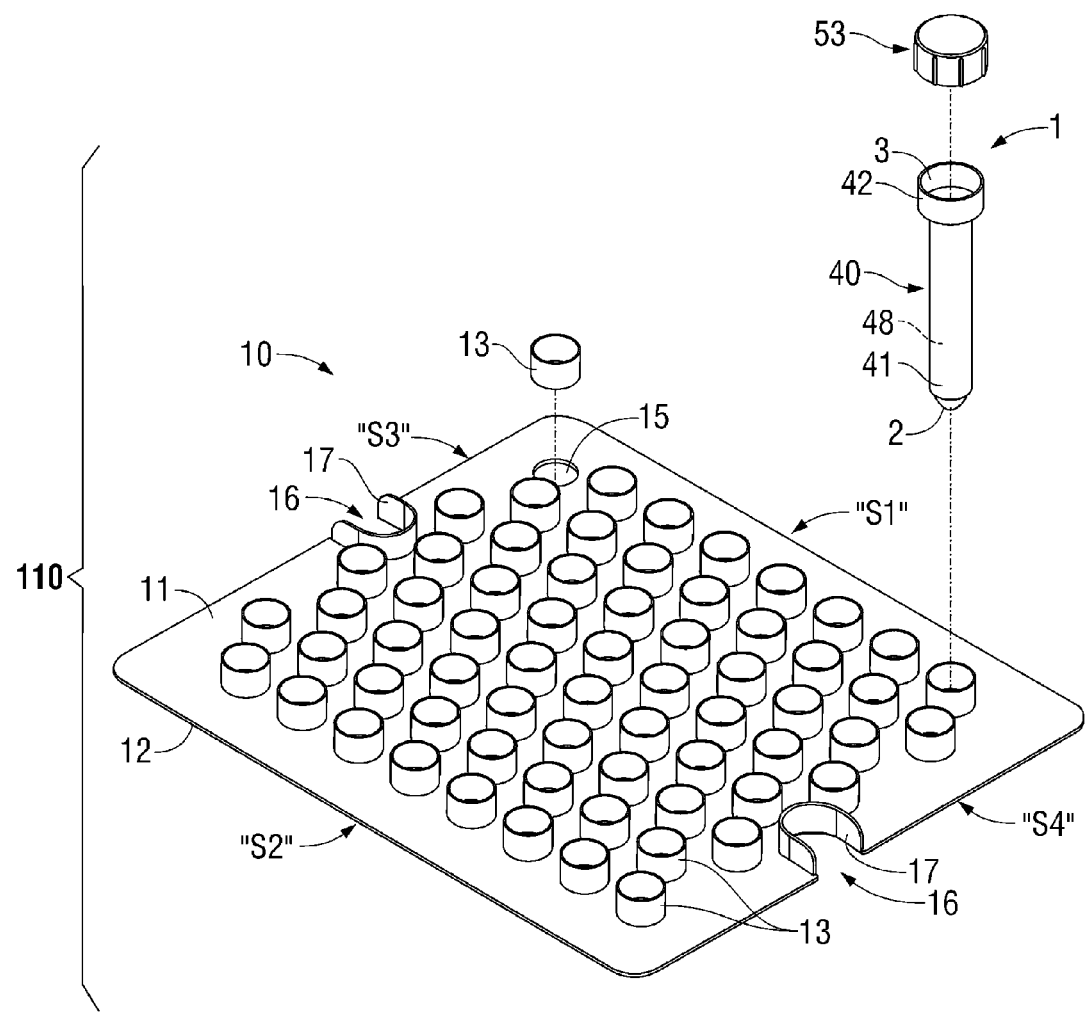
FIG. 1 is a perspective view of a syringe assembly carrier with parts separated according to an embodiment of the present disclosure.

Hereinafter, embodiments of a syringe assembly and a syringe assembly carrier suitable for syringe filling and distribution of syringe assemblies are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". As it is used in this description, "plastic" generally refers to any of a wide variety of resins or polymers with different characteristics and uses.

Embodiments of the presently-disclosed syringe assembly are suitable for use as disposable syringes and prefilled syringes. Embodiments of the presently-disclosed syringe assembly carrier allow syringes to be assembled, sterilized and distributed in a structured configuration suitable for presentation to automated syringe-filling operations. The teachings of the present disclosure may apply to a variety of syringe assemblies that include a selectively attachable/detachable plunger assembly.

FIG. 1 illustrates one embodiment of the presently-disclosed syringe assembly carrier shown generally as 110. Syringe assembly carrier 110 includes a plurality of syringe wells 1, a syringe-well holding fixture 10, an array of openings 15 defined in syringe-well holding fixture 10, and a plurality of annular mounting flanges 13 individually associated with openings 15 and configured to receive syringe wells 1. In some embodiments, each of the annular mounting flanges 13 is configured to releaseably or semi-permanently receive a syringe well 1. In some embodiments, each of the annular mounting flanges 13 is configured to permanently receive a syringe well 1. Each of the plurality of syringe wells 1 includes an interior cavity 48 of sufficient diameter to removeably receive a syringe assembly (e.g., 100 shown in FIGS. 2 and 3). A plurality of sealing caps 53 may be provided for assembly with the syringe wells 1.

The plurality of openings 15 and the annular mounting flanges 13 are generally arranged in a pattern of rows and/or columns. Alternatively, other patterns are envisioned. Openings 15 and the annular mounting flanges 13 may be arranged as nested rows and columns. Openings 15 may be arranged in a series of rows and/or columns, and may be uniformly spaced apart. The syringe-well holding fixture 10 and annular mounting flanges 13 may be integrally formed as a unitary structure. The number, shape and size of the openings 15 and the annular mounting flanges 13 may be varied from the configuration depicted in FIGS. 1 through 3. Openings 15 may have any configuration suitable for a specific purpose. For example, openings 15 may be shaped as circles, square, triangles, octagons and the like.

Syringe-well holding fixture 10 and the syringe wells 1 may be separately formed by injection-molding devices from suitable polymeric materials, e.g., polyolefins such as polypropylene. In some embodiments, one or more syringe wells 1 and/or the syringe-well holding fixture 10 may be transparent or semi-transparent, which may allow a user to visually inspect the syringe assemblies 100 disposed within the syringe wells 1. Alternatively, one or more syringe wells 1 and/or the syringe-well holding fixture 10 may be opaque, e.g., to protect the contents of the syringe wells 1 against exposure to light.

Figure 2:
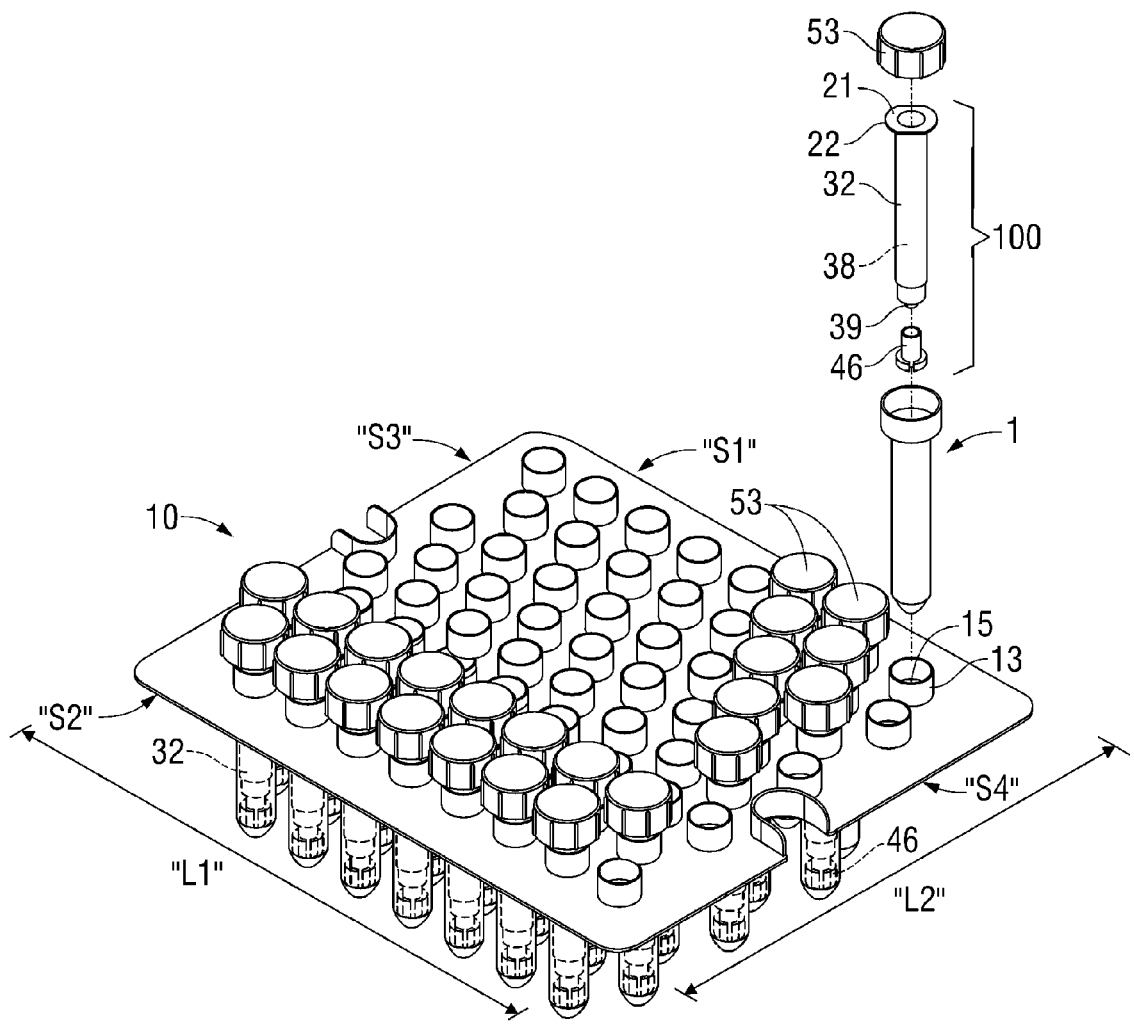
FIG. 2 is a perspective view of an embodiment of a syringe assembly with parts separated and an embodiment of an opaque, syringe-well holding fixture shown in a partially-filled configuration with syringe assemblies (in phantom lines) disposed in transparent syringe wells in accordance with the present disclosure.

In the embodiment illustrated in FIG. 2, each of the syringe wells 1 is transparent and the syringe-well holding fixture 10 is opaque. In the embodiment illustrated in FIG. 3, each of the syringe wells 1 and the syringe-well holding fixture 10 is transparent. It is contemplated and within the scope of the present disclosure that the presently-disclosed syringe-well holding fixture 10 may be provided with various configurations of opaque syringe wells 1 and/or transparent syringe wells 1, which may accommodate filled and/or unfilled syringe assemblies therein.

Syringe-well holding fixture 10 includes an upper surface 11, which may be flat or substantially flat, and a lower surface 12. In some embodiments, the fixture 10 has a generally rectangular shape, which may be formed from a first side "S1", a second side "S2", a third side "S3" and a fourth side "S4". It is also envisioned that the fixture may assume other configurations, e.g., circular, square, etc. As shown in FIG. 2, the first side "S1" and the second side "S2" have a suitable length "L1", and the third side "S3" and the fourth side "S4" have a suitable length "L2". In some embodiments, the first side "S1" and the second side "S2" are disposed perpendicular to the third side "S3" and the fourth side "S4", Syringe-well holding fixture 10 may be fabricated from a suitably rigid material. In some embodiments, the fixture 10 is formed substantially or entirely from a polymeric material, e.g., plastic.

In some embodiments, one or more cut-out portions 16 (FIG. 1) are defined in the syringe-well holding fixture 10, e.g., to facilitate gripping the syringe assembly carrier 110 and/or to allow the fixture 10 to be positionable in a predetermined orientation for syringe filling operations. In one embodiment, fixture 10 includes two cut-out portions 16 disposed on opposite sides of the fixture 10, e.g., the third side "S3" and the fourth side "S4". Syringe assembly carrier 110 may include one or more rib elements 17 (FIG. 1), which may be disposed in proximity to the one or more cut-out portions 16 and configured to provide structural support and rigidity to the syringe-well holding fixture 10. Rib elements 17 may be coupled to the upper surface 11 of the fixture 10 and/or the lower surface 12 of the fixture 10. In the embodiment illustrated in FIGS. 1 through 3, the syringe-well holding fixture 10 includes two cut-out portions 16 and two rib elements 17 coupled to the upper surface 11, wherein each rib element 17 has a generally U-like shape and is disposed in proximity to a corresponding one of the cut-out portions 16. The number, size, shape and relative spacing of the cut-out portions 16 and rib elements 17 may be varied from the configuration depicted in FIG. 1.

Referring again to FIG. 1, each of the plurality of syringe wells 1 includes an open end 3, a closed end 2, and a sleeve body 40, wherein an interior cavity 48 is defined within the sleeve body 40 between the open end 3 and the closed end 2. Sleeve body 40 may include a first portion 41, e.g., a lower portion, having a generally cylindrical configuration, and a second portion 42, e.g., an upper portion. Sleeve body 40 may be configured to press-fit, snap, or otherwise seal into the annular mounting flanges 13 of syringe-well holding fixture 10. In some embodiments, the sleeve body 40 is releaseably or semi-permanently coupleable to the annular mounting flanges 13. In other embodiments, the sleeve body 40 is permanently coupleable to the annular mounting flanges 13. The second portion 42 of the sleeve body 40 may be configured to receive a sealing cap 53. The closed end 2 of the syringe wells 1 may have a rounded shape, or other suitable shape, such as triangular, square, octagon and the like. In some embodiment the sleeve body 42 may have differing cross sectional areas along its length. For example the cross sectional area of the upper portion 42 of the sleeve may be larger than the cross sectional area of the lower portion 41 of the sleeve.

FIG. 2 illustrates one embodiment of the presently-disclosed syringe assembly shown generally as 100 and an embodiment of syringe assembly carrier 110. In the embodiment illustrated in FIG. 2, the syringe-well holding fixture 10 is opaque and each of the plurality of syringe wells 1 is transparent.

Syringe assembly 100 may be a single-use assembly, which is disposable after use on a subject. Syringe assembly 100 is suitable for use in pre-filled applications and includes a syringe body 32, a flange 22, and a tip cap 46. Syringe body 32 defines a fluid chamber or reservoir 38 and includes a distally-positioned nozzle portion or tip 39, which is disposed in fluid communication with the fluid reservoir 38. Tip cap 46 includes an open end configured to be releaseably coupleable with the distal end of the nozzle portion or tip 39. In some embodiments, the syringe body 32 is made of plastic, e.g., transparent polypropylene. Syringe body 32 may be constructed of nearly any polymeric or glass material. A plunger assembly (not shown) may be provided for assembly with the syringe body 32.

Fluid reservoir 38 is generally configured to contain a material to be dispensed and/or aspirated. In embodiments, the fluid reservoir 38 may have an internal volume of about 0.3 ml (milliliters) to about 100 ml, although other fluid reservoir volumes are envisioned.

Adjacent the proximal end of the syringe body 32 is a peripheral flange 22 that includes a proximal end 21 and extends perpendicularly beyond the periphery of the syringe body 32. Syringe flange 22 may be integrally formed with the syringe body 32.

Figure 3:
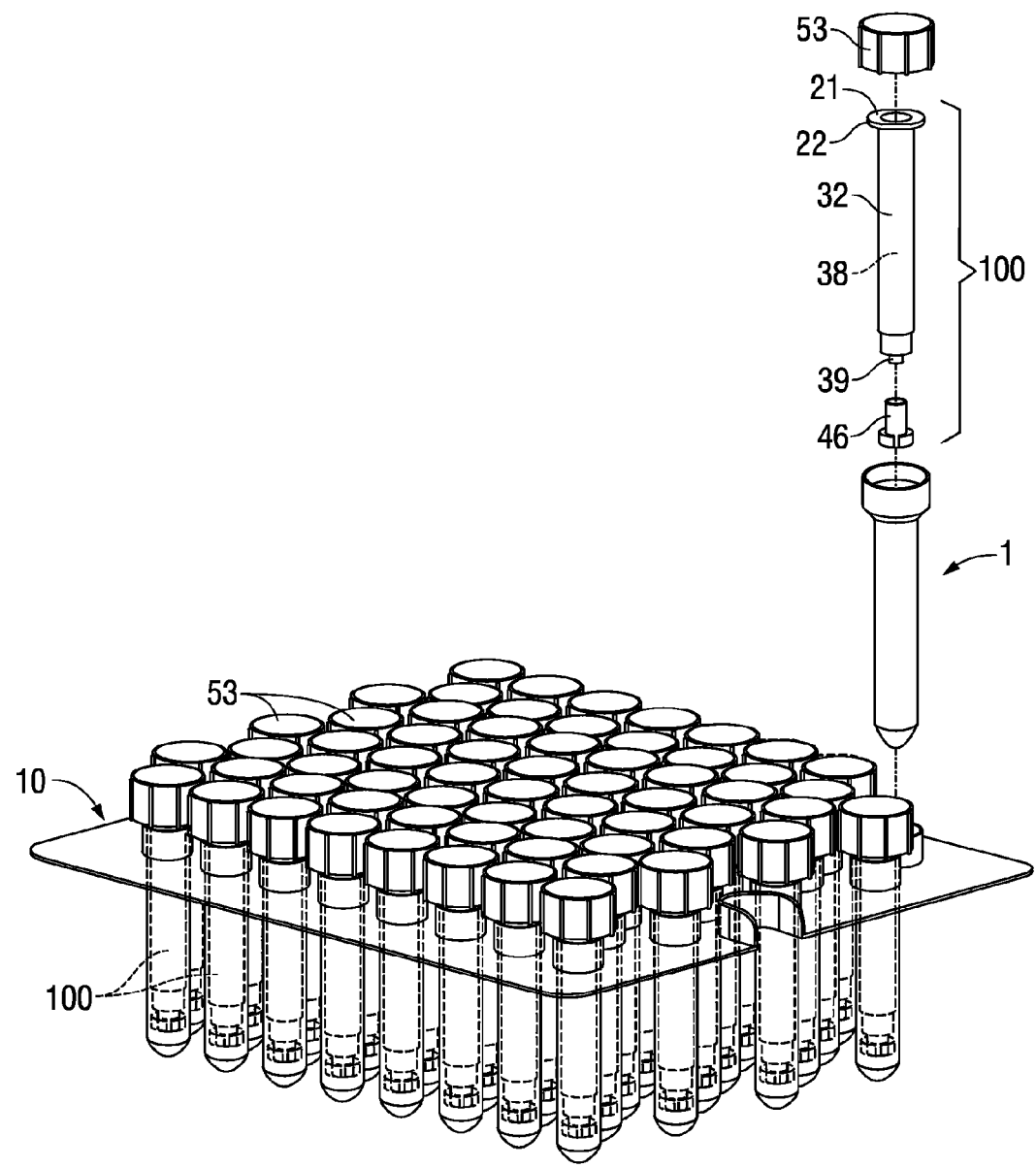
FIG. 3 is a perspective view of a syringe assembly as shown in FIG. 2 and an embodiment of a transparent, syringe-well holding fixture shown in a substantially-filled configuration with syringe assemblies (in phantom lines) disposed in transparent syringe wells according to an embodiment of the present disclosure.

In FIG. 3, a plurality of the syringe assemblies 100 are shown (in phantom lines) disposed within syringe wells 1, wherein each of the syringe wells 1 is provided with a sealing cap 53 and is coupled to the syringe-well holding fixture 10 of the syringe assembly carrier 110. Syringe assemblies 100 are oriented generally perpendicularly to the generally planar upper surface 11 of the syringe-well holding fixture 10 and are loaded into the syringe-well holding fixture 10 such that the distal end of the syringe body 32, covered by the tip cap 46, faces the closed end 2 of the syringe well 1 and the proximal end 21 of the syringe flange 22 faces upward.

In some embodiments, fluid reservoir 38 of the syringe assembly 100 is filled with a solution (not shown) before the syringe assembly 100 is loaded into a syringe well 1 of the syringe assembly carrier 110. In other embodiments, the syringe assembly 100 is loaded into a syringe well 1 before the fluid reservoir 38 is filled with a solution. In certain applications, syringe assembly 100 may contain a flushing solution, e.g., saline or the like. Alternatively, syringe assembly 100 may contain medicinals, including antibiotics, pain medication, therapeutic drugs, heparin or the like.

Sealing caps 53 may be applied to the syringe wells 1 after the syringe assemblies 100 are loaded into the syringe well 1, sterilized, and/or filled with a solution. Sealing caps 53 are configured to be releaseably coupleable to the upper portion 42 of syringe wells 1 by any suitable manner of releasable connection, such as, snap-fit, press-fit, screw-fit, bayonet-fit, friction-fit, releasable adhesive, or other releasable configuration.

In some embodiments in which sealing caps are not utilized, a sterile barrier film (not shown) may be provided, wherein the barrier film is configured to cover the open ends 3 of the syringe wells 1. The barrier film may be adhered by an adhesive layer (not shown), or other suitable manner of adhesion, welding or the like. The barrier film may be applied to cover the open ends 3 of the syringe wells 1 after the syringe assemblies 100 are loaded into the syringes well 1, sterilized, and/or filled with a solution.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A syringe assembly carrier, comprising:
    a plurality of syringe wells, each including an open end and a closed end, wherein each of the plurality of syringe wells is configured to removeably receive a syringe assembly;
    a syringe well holding fixture including an upper surface;
    a plurality of openings defined in the syringe well holding fixture; and
    a plurality of annular mounting flanges coupled to the upper surface, wherein each of the plurality of annular mounting flanges is individually associated with a different opening in the syringe well holding fixture and configured to removeably receive one of said syringe wells.

2. The syringe assembly carrier of claim 1, wherein each syringe well of the plurality of syringe wells further includes:
    a sleeve body disposed between the open end and the closed end; and
    a cavity defined within the sleeve body configured to receive the syringe assembly therein.

3. The syringe assembly carrier of claim 2, wherein the sleeve body includes a first portion having a generally cylindrical shape and a second portion configured to receive a sealing cap.

4. The syringe assembly carrier of claim 3, wherein the first portion of the sleeve body is configured to receive a syringe body of the syringe assembly therein.

5. The syringe assembly carrier of claim 4, wherein the second portion of the sleeve body is configured to receive a syringe flange of the syringe assembly therein.

6. The syringe assembly carrier of claim 5, further comprising:
    a plurality of sealing caps configured to be releaseably coupleable to the second portion of the sleeve body.

7. The syringe assembly carrier of claim 2, further comprising:
    a sterile barrier film configured to cover the open end of the plurality of syringe wells.

8. The syringe assembly carrier of claim 1, wherein each syringe well of the plurality of syringe wells is transparent.

9. The syringe assembly carrier of claim 8, wherein the syringe-well holding fixture is transparent.

* * * * *